(12) United States Patent
Li

(10) Patent No.: US 8,093,428 B2
(45) Date of Patent: Jan. 10, 2012

(54) SYNTHESIS OF QUATERNARY SALT COMPOUNDS

(75) Inventor: Xun Li, New Hope, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 488 days.

(21) Appl. No.: 12/255,769

(22) Filed: Oct. 22, 2008

(65) Prior Publication Data

US 2009/0112003 A1 Apr. 30, 2009

Related U.S. Application Data

(60) Provisional application No. 60/982,815, filed on Oct. 26, 2007.

(51) Int. Cl.
*C07C 211/00* (2006.01)
(52) U.S. Cl. ........................................... 564/306
(58) Field of Classification Search .................. 564/306
See application file for complete search history.

(56) References Cited

U.S. PATENT DOCUMENTS

| | | | |
|---|---|---|---|
| 4,450,174 A | 5/1984 | Green et al. | |
| 4,845,289 A | 7/1989 | Ries et al. | |
| 6,172,061 B1 | 1/2001 | Nishimura et al. | |
| 6,268,354 B1 | 7/2001 | Nishimura et al. | |
| 6,444,846 B1 | 9/2002 | Smith et al. | |
| 2006/0029337 A1 | 2/2006 | Vancoille et al. | |
| 2006/0293379 A1 | 12/2006 | Lagu et al. | |
| 2009/0112004 A1 | 4/2009 | Palmer et al. | |

FOREIGN PATENT DOCUMENTS

| | | |
|---|---|---|
| CN | 1680278 A | 10/2005 |
| EP | 288857 A | 11/1988 |
| WO | WO 00/10965 A | 3/2000 |

OTHER PUBLICATIONS

Nebergall et al, College Chemistry with Qualitative Analysis, 1980, p. 89, pp. 3.*
Bolt, "Mechanisms of Carcinogenicity of Methyl Halides", *Critical Reviews in Toxicology*, 1993, 23(3), 237-253.
Hashimoto et al., "Process Development of 4-[N-Methyl-N-)tetrahydropyran-4-yl)aminomethyl]aniline Dehydrochloride: A Key Intermediate for TAK-779 a Small-Molecule Nonpeptide CCR5 Antagonist", *Organic Process Research and Development*, 2002, 6, 70-73.
Ikemoto et al., "Development of a New Synthetic Route of a Non-Peptide CCR5 Antagonist, TAK-779, for Large Scale Preparation", *Organic Process Research and Development*, 2000, 4, 520-525 (XP002513618).
Ikemoto et al., "Practical Synthesis of an Orally Active CCR5 Antagonist, 7-{4-[2-(butoxy)-ethoxy-phenyl}-N-(4-{methyl-(tetrahydro-2H-pyran-4-yl)amino}methyl]phenyl)-1-propyl-2,3-dihydro-1H-1-benzazepine-4-carboxamide", *Organic Process Research and Development*, 2005, 9, 168-173).
Ikemoto et al., "Convenient, Efficient Synthesis of TAK-779, a Non-Peptide CCR5 Antagonist: Development of Preparation of Various Ammonium Salts using Trialkylphosphite and N-Halogenosuccinimide", *Tetrahedron*, 2001, 57, 1525-1529.
Shiraishi et al., "Discovery of Novel, Potent, and Selective Small-Molecule CCR5 Antagonists as Anti-HIV Agents: Synthesis and Biological Evaluation of Anilide Derivatives with a Quaternary Ammonium Moiety", *J.Med.Chem.*, 2000, 43, 2049-2063 (XP002951542).

* cited by examiner

*Primary Examiner* — Taylor Victor Oh

(57) ABSTRACT

The present invention is directed to a process, having a reduced environmental impact, for preparing phenylamino substituted quaternary salt compounds that are CCR2 antagonists.

12 Claims, No Drawings

SYNTHESIS OF QUATERNARY SALT COMPOUNDS

CROSS-REFERENCE TO RELATED APPLICATIONS

This Application claims priority to U.S. Provisional Patent Application No. 60/982,815, filed Oct. 26, 2007, which is hereby incorporated by reference in its entirety.

FIELD OF THE INVENTION

The present invention is directed to a process for preparing quaternary salt compounds which are antagonists to the chemoattractant cytokine receptor 2 (CCR2). More particularly, the process is directed to a synthesis of a phenylamino substituted quaternary salt CCR2 antagonist compound wherein said synthesis has a reduced environmental impact.

BACKGROUND OF THE INVENTION

The design of an optimized chemical manufacturing process is very often a process as well, keeping in mind the goals of synthetic efficiency, waste reduction and use of materials having a reduced health risk. A manufacturing synthesis having a reduced environmental impact may employ a safer synthetic design by using minimally hazardous reagents and solvents, thus providing a new, more efficient and cost-effective process with positive environmental and economic impacts. The process of the present invention, while providing a pharmaceutically useful series of compounds, eliminates the use of known mutagenic reagents and chlorinated solvents. Accordingly, the synthesis of the present invention may reduce overall economic and environmental impact by using a reduced amount of reagents and solvents as well as less hazardous reagents and solvents, thereby reducing attendant disposal costs and the total cost of goods.

Patent Application CN2005-10023182 describes a method for producing quaternary ammonium salts by reacting trialkylamine with a halohydrocarbon at a molar ratio of 1:1 with linear or branched $C_{10-22}$alkyl monohydric alcohols under a pressure of from 0 to 980 KPa(g) at a temperature of from 10 to 140° C. for a period of from 8 to 240 hours.

Patent Application EP0288857A3 describes quaternary ammonium halides prepared by the addition reaction of tertiary amines with alkyl halides in molar ratios of from 1:3 to 1:8 at a temperature of from 50 to 150° C. under elevated pressure in the absence of solvents.

U.S. Pat. No. 4,450,174 describes antimicrobial quaternary ammonium compounds, particularly decyl alkyl dimethylammonium chloride, prepared by the classical alkylation reaction of a tertiary amine with a primary alkyl halide, particularly didecyl methylamine with methylchloride gas.

U.S. Pat. No. 4,845,289 describes a process for the removal or reduction of residual trimethyl amine odor resulting from the quaternization of a halogen containing precursor with trimethyl amine by reacting the residual trimethyl amine with at least an equivalent amount of methyl chloride at a temperature of at least 50° C.

U.S. Pat. No. 6,444,846 describes a process for preparing a tetraalkyl ammonium halide using a catalytic amount of acetonitrile in a reaction under pressure and at an elevated temperature of an alkyl halide and a trialkyl amine and in which tetrafluoroborate can be subsequently prepared.

United States Patent Publication 2006/0293379, incorporated herein by reference in its entirety and for all purposes, describes CCR2 antagonist compounds of Formula (I) that may be prepared using the process of the present invention. Additionally, all other documents cited herein are incorporated by reference in their entirety and for all purposes.

The compound of Formula (Ia) has also been disclosed in U.S. Patent Publication 2006/0293379 and referred to as [4-(3,4-dichloro-benzoylamino)-benzyl]-dimethyl-(tetrahydropyran-4-yl)-ammonium chloride Compound 17 and synthesized as disclosed in Example 1 of same.

SUMMARY OF THE INVENTION

The present invention broadly relates to a process for preparing a quaternary salt compound of Formula (I):

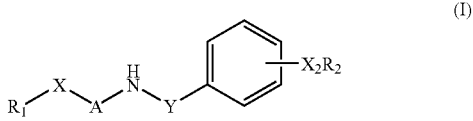

(I)

wherein $R_1$, X, A, Y and $X_2R_2$ are as defined herein.

The present invention also relates to a process for preparing a quaternary salt compound of Formula (Ia):

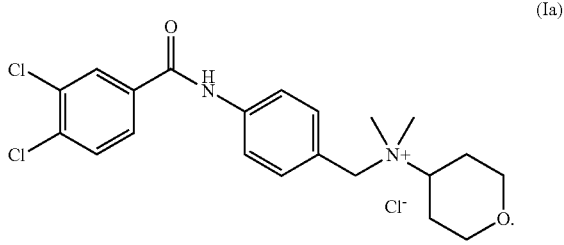

(Ia)

DETAILED DESCRIPTION OF THE INVENTION

The present invention broadly relates to a process for preparing a quaternary salt compound of Formula (I):

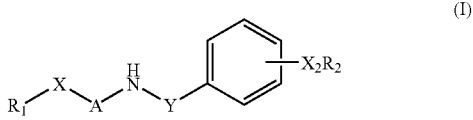

(I)

wherein
A is carbonyl, thiocarbonyl or sulfonyl;
X is a bond or —CH=CH—;
$R_1$ is selected from aryl, $C_5$-$C_{15}$cycloalkyl or heterocyclyl,
wherein aryl is optionally substituted with one or more lower alkyl, —$(CH_2)_n$—$CF_3$, lower alkoxy, alkoxycarbonyl, cyano, halogen or phenyl optionally substituted by lower alkyl, —$(CH_2)_n$—$CF_3$, lower alkoxy, alkoxycarbonyl, cyano or halogen,
wherein $C_5$-$C_{15}$cycloalkyl is optionally substituted with one or more lower alkyl, —$(CH_2)_n$—$CF_3$, lower alkoxy, aryl, halogen-substituted aryl, alkoxycarbonyl, cyano or halogen, or
wherein heterocyclyl is optionally substituted with one or more lower alkyl, —$(CH_2)_n$—$CF_3$, lower alkoxy, aryl, aryl-lower alkyl, halogen-substituted aryl, alkoxycarbonyl, cyano or halogen; and wherein n is 0, 1, 2, 3 or 4;

Y is a bond or —$CH_2$—;

$X_2$ is —$(CH_2)_m$—, wherein m is 1 or 2;

$R_2$ is —$N^+(R_4R_5)$—$ZR_3$;

Z is —$(CH_2)_p$— wherein p is 0, 1 or 2;

$R_3$ is selected from aryl, $C_5$-$C_{15}$cycloalkyl or heterocyclyl, wherein aryl is optionally substituted with one or more lower alkyl, —$(CH_2)_n$—$CF_3$, lower alkoxy, aryl, halogen-substituted aryl, alkoxycarbonyl, cyano or halogen, wherein $C_5$-$C_{15}$cycloalkyl is optionally substituted with one or more lower alkyl, —$(CH_2)_n$—$CF_3$, lower alkoxy, aryl, halogen-substituted aryl, alkoxycarbonyl, cyano or halogen, or wherein heterocyclyl is optionally substituted with one or more lower alkyl, —$(CH_2)_n$—$CF_3$, lower alkoxy, aryl, halogen-substituted aryl, alkoxycarbonyl, cyano or halogen; and wherein, when heterocyclyl is attached via a carbon atom ring member and a heteroatom ring member is adjacent to said carbon atom, then p is 1 or 2; and $R_4$ and $R_5$ are each individually lower alkyl or lower alkenyl; or alternatively, $R_4$ and $R_5$ combine with the nitrogen atom of Formula (I) to form a heterocyclyl ring of 5 to 9 total ring atoms optionally containing one of an oxygen or sulfur ring atom, wherein the heterocyclyl ring nitrogen atom is substituted with one of lower alkyl or lower alkenyl to form a quaternary salt, and wherein—$ZR_3$ is absent and the heterocyclyl ring is optionally substituted with aryl optionally substituted with one or more lower alkyl, —$(CH_2)_n$—$CF_3$, lower alkoxy, aryl, halogen-substituted aryl, alkoxycarbonyl, cyano or halogen;

according to Scheme A, comprising the steps of:

Scheme A

Step A. reacting a Compound A1 hydrochloride salt with an aldehyde or ketone Compound A2 to provide a Compound A3:

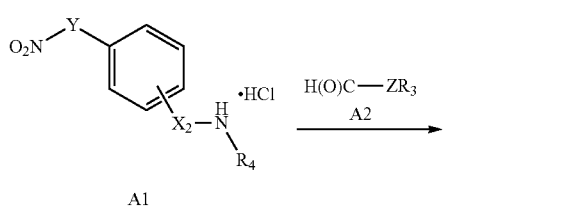

Step B. reacting Compound A3 in the presence of a metallation reagent to provide a Compound A4:

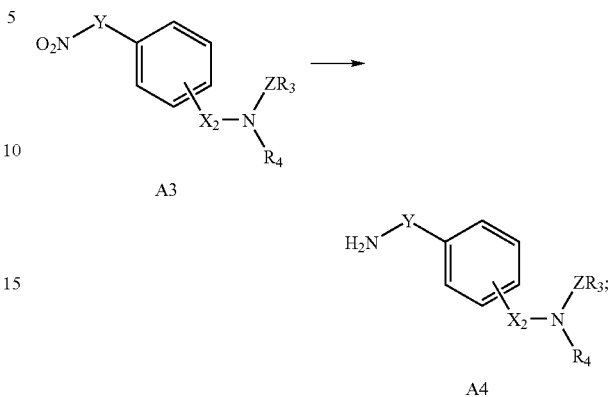

Step C. reacting Compound A4 with a Compound A5 (wherein Q represents a leaving group such as chloride or hydroxy) to provide a Compound A6:

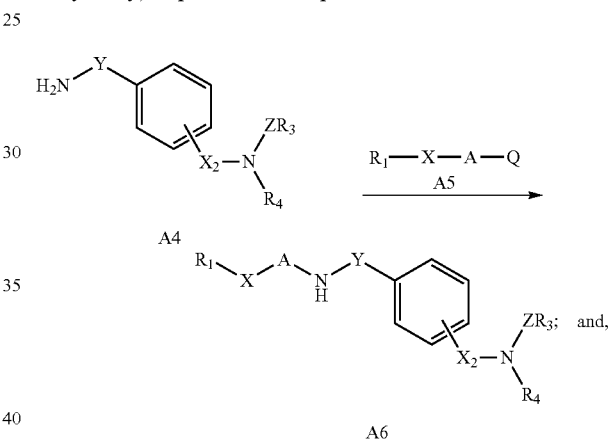

Step D. reacting Compound A6 with a chlorinated alkyl Compound A7 to provide a quaternary salt Compound A8, representative of the compound of Formula (I):

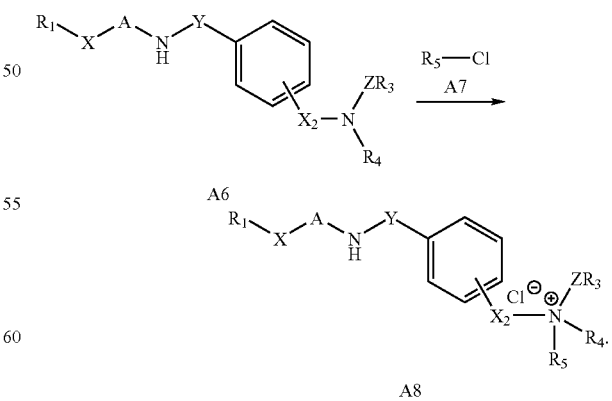

In Step A., the reaction illustrated is adapted from Shiroshi, et al., *J. Med. Chem.,* 2000, 43, 2049 and Hashimoto et al., *Org. Proc. R&D,* 2002, 6, 70).

In Step A., the reaction of Compound A1 and Compound A2 is carried out in a solvent such as $CH_2Cl_2$ and the like, followed by the stepwise addition of $Et_3N$ and $NaB(OAc)_3H$.

In Step B., the reaction of Compound A3 uses a metallation reducing reagent such as $SnCl_2.2H_2O$ in conc. HCl and the like in a solvent such as THF and the like.

In Step C., the reaction of Compound A4 and Compound A5 is carried out in a solvent mixture such as $Et_3N$ in THF and the like.

In Step D., the reaction of Compound A6 and Compound A7 is carried out by adding Compound A7 to a solution of Compound A6 in a solvent under pressure and at an elevated temperature.

The solvent used in Step D. is selected from the group consisting of n-BuOH, toluene, IPA, EtOH, acetone, MeCN, DMF, THF and the like and mixtures thereof, wherein the reaction conditions include an elevated temperature and pressure. More specifically, the choice of solvent used depends on the reaction temperature and pressure conditions, wherein the temperature is less than the boiling point of the solvent at a particular pressure.

Furthermore, where the temperature and pressure chosen depend on the equipment used, the scope of the process parameters is intended to include all temperature and pressure configurations known to those skilled in the art which may be used to achieve the purpose of the present invention. For example, the temperature may be in a range of from about 20° C. to about 200° C., or in a range of from about 50° C. to about 120° C., or in a range of from about 80° C. to about 100° C. and or about 100° C.

In embodiments of the present invention, the solvent used in Step D is selected from the group consisting of n-BuOH and toluene.

In embodiments of the present invention, the reaction pressure used in Step D. may be in a range of from about 15 psi to about 200 psi, or from about 15 psi to about 100 psi, or from about 15 psi to about 50 psi, or from about 15 psi to about 25 psi, or from about 20 psi to about 25 psi, or about 22 psi.

In embodiments of the present invention, the molar ratio of Compound A6:Compound A7 is from about 1:3 to about 1:8; or, from about 1:3 to about 1:5; or, about 1:3.

U.S. Patent Publication 2006/0293379 discloses the following compounds as quaternary iodide salt compounds. The following quaternary chloride salt compounds representative of Formula (I) may be prepared according to the process of the present invention and are selected from the group consisting of:

| Cpd | Name |
|---|---|
| 1 | (4-{[3-(3-bromo-phenyl)-acryloylamino]-methyl}-benzyl)-cyclohexyl-dimethyl-ammonium chloride, |
| 2 | {4-[(3-bromo-benzoylamino)-methyl]-benzyl}-cyclohexyl-dimethyl-ammonium chloride, |
| 3 | cyclohexyl-dimethyl-{4-[(3-trifluoromethyl-benzoylamino)-methyl]-benzyl}-ammonium chloride, |
| 4 | (4-{[3-(3,4-dichloro-phenyl)-acryloylamino]-methyl}-benzyl)-dimethyl-(tetrahydro-pyran-4-yl)-ammonium chloride, |
| 5 | (4-{[3-(3-bromo-phenyl)-acryloylamino]-methyl}-benzyl)-dimethyl-(tetrahydro-pyran-4-yl)-ammonium chloride, |
| 6 | (4-benzoylamino-benzyl)-dimethyl-(tetrahydro-pyran-4-yl)-ammonium chloride, |
| 7 | [3-(3,4-dichloro-benzoylamino)-benzyl]-dimethyl-(tetrahydro-pyran-4-yl)-ammonium chloride, |
| 8 | [3-(3-bromo-benzoylamino)-benzyl]-dimethyl-(tetrahydro-pyran-4-yl)-ammonium chloride, |
| 9 | [4-(2,3-dichloro-benzoylamino)-benzyl]-dimethyl-(tetrahydro-pyran-4-yl)-ammonium chloride, |
| 10 | [4-(2,4-dichloro-benzoylamino)-benzyl]-dimethyl-(tetrahydro-pyran-4-yl)-ammonium chloride, |
| 11 | [4-(2,5-dichloro-benzoylamino)-benzyl]-dimethyl-(tetrahydro-pyran-4-yl)-ammonium chloride, |
| 12 | [4-(2,6-dichloro-benzoylamino)-benzyl]-dimethyl-(tetrahydro-pyran-4-yl)-ammonium chloride, |
| 13 | [4-(2-chloro-benzoylamino)-benzyl]-dimethyl-(tetrahydro-pyran-4-yl)-ammonium chloride, |
| 14 | bicyclo[2.2.1]hept-2-yl-[4-(3,4-dichloro-benzoylamino)-benzyl]-dimethyl-ammonium chloride, |
| 15 | (2S)-[4-(3,4-dichloro-benzoylamino)-benzyl]-dimethyl-(tetrahydro-furan-2-ylmethyl)-ammonium chloride, |
| 16 | (2R)-[4-(3,4-dichloro-benzoylamino)-benzyl]-dimethyl-(tetrahydro-furan-2-ylmethyl)-ammonium chloride, |
| 18 | [4-(3,4-dichloro-benzoylamino)-benzyl]-dimethyl-(tetrahydro-pyran-4-ylmethyl)-ammonium chloride, |
| 19 | [4-(3,4-dichloro-benzoylamino)-benzyl]-dimethyl-(tetrahydro-thien-3-yl)-ammonium chloride, |
| 20 | [4-(3,4-dichloro-benzoylamino)-benzyl]-dimethyl-(tetrahydro-thiopyran-4-yl)-ammonium chloride, |
| 21 | [4-(3,4-dichloro-benzoylamino)-benzyl]-ethyl-methyl-(tetrahydro-pyran-4-yl)-ammonium chloride, |
| 22 | [4-(3,4-dichloro-benzoylamino)-benzyl]-methyl-propyl-(tetrahydro-pyran-4-yl)-ammonium chloride, |
| 23 | [4-(3,5-dichloro-benzoylamino)-benzyl]-dimethyl-(tetrahydro-pyran-4-yl)-ammonium chloride, |
| 24 | [4-(3-bromo-benzoylamino)-benzyl]-dimethyl-(tetrahydro-pyran-4-yl)-ammonium chloride, |
| 25 | [4-(3-chloro-2-methyl-benzoylamino)-benzyl]-dimethyl-(tetrahydro-pyran-4-yl)-ammonium chloride, |

| Cpd | Name |
|---|---|
| 26 | [4-(3-chloro-4-fluoro-benzoylamino)-benzyl]-dimethyl-(tetrahydro-pyran-4-yl)-ammonium chloride, |
| 27 | [4-(3-chloro-4-methoxy-benzoylamino)-benzyl]-dimethyl-(tetrahydro-pyran-4-yl)-ammonium chloride, |
| 28 | [4-(3-chloro-4-methyl-benzoylamino)-benzyl]-dimethyl-(tetrahydro-pyran-4-yl)-ammonium chloride, |
| 29 | [4-(3-chloro-benzoylamino)-benzyl]-dimethyl-(tetrahydro-pyran-4-yl)-ammonium chloride, |
| 30 | [4-(3-cyano-benzoylamino)-benzyl]-dimethyl-(tetrahydro-pyran-4-yl)-ammonium chloride, |
| 31 | [4-(3-methoxy-benzoylamino)-benzyl]-dimethyl-(tetrahydro-pyran-4-yl)-ammonium chloride, |
| 32 | [4-(4-chloro-2-methyl-benzoylamino)-benzyl]-dimethyl-(tetrahydro-pyran-4-yl)-ammonium chloride, |
| 33 | [4-(4-chloro-3-trifluoromethyl-benzoylamino)-benzyl]-dimethyl-(tetrahydro-pyran-4-yl)-ammonium chloride, |
| 34 | [4-(4-chloro-benzoylamino)-benzyl]-dimethyl-(tetrahydro-pyran-4-yl)-ammonium chloride, |
| 35 | [4-(5-chloro-2-methyl-benzoylamino)-benzyl]-dimethyl-(tetrahydro-pyran-4-yl)-ammonium chloride, |
| 36 | {2-[4-(3,4-dichloro-benzoylamino)-phenyl]-ethyl}-dimethyl-(tetrahydro-pyran-4-yl)-ammonium chloride, |
| 37 | {2-[4-(3-bromo-benzoylamino)-phenyl]-ethyl}-dimethyl-(tetrahydro-pyran-4-yl)-ammonium chloride, |
| 38 | {3-[3-(3-bromo-phenyl)-acryloylamino]-benzyl}-dimethyl-(tetrahydro-pyran-4-yl)-ammonium chloride, |
| 39 | {4-[(3,4-dichloro-benzoylamino)-methyl]-benzyl}-dimethyl-(tetrahydro-pyran-4-yl)-ammonium chloride, |
| 40 | {4-[3-(3,4-dichloro-phenyl)-acryloylamino]-benzyl}-dimethyl-(tetrahydro-pyran-4-yl)-ammonium chloride, |
| 41 | {4-[3-(3,4-dichloro-phenyl)-acryloylamino]-benzyl}-dimethyl-(tetrahydro-thiopyran-4-yl)-ammonium chloride, |
| 42 | {4-[3-(3,5-difluoro-phenyl)-acryloylamino]-benzyl}-dimethyl-(tetrahydro-pyran-4-yl)-ammonium chloride, |
| 43 | {4-[3-(3-bromo-phenyl)-acryloylamino]-benzyl}-dimethyl-(tetrahydro-pyran-4-yl)-ammonium chloride, |
| 44 | {4-[3-(3-bromo-phenyl)-acryloylamino]-benzyl}-dimethyl-(tetrahydro-thiopyran-4-yl)-ammonium chloride, |
| 45 | {4-[3-(3-chloro-phenyl)-acryloylamino]-benzyl}-dimethyl-(tetrahydro-pyran-4-yl)-ammonium chloride, |
| 46 | {4-[3-(3-fluoro-phenyl)-acryloylamino]-benzyl}-dimethyl-(tetrahydro-pyran-4-yl)-ammonium chloride, |
| 47 | {4-[3-(4-bromo-phenyl)-acryloylamino]-benzyl}-dimethyl-(tetrahydro-pyran-4-yl)-ammonium chloride, |
| 48 | 1-(4-{[3-(3,4-dichloro-phenyl)-acryloylamino]-methyl}-benzyl)-1-methyl-piperidinium chloride, |
| 49 | 1-(4-{[3-(3-bromo-phenyl)-acryloylamino]-methyl}-benzyl)-1-methyl-piperidinium chloride, |
| 50 | 1-[4-(3,4-dichloro-benzoylamino)-benzyl]-1-methyl-piperidinium chloride, |
| 51 | 1-[4-(3,4-dichloro-benzoylamino)-benzyl]-1-methyl-pyrrolidinium chloride, |
| 52 | 1-{3-[3-(3-bromo-phenyl)-acryloylamino]-benzyl}-1-methyl-piperidinium chloride, |
| 53 | 1-{4-[3-(3,4-dichloro-phenyl)-acryloylamino]-benzyl}-1-methyl-piperidinium chloride, |
| 54 | 1-{4-[3-(3,4-dichloro-phenyl)-acryloylamino]-benzyl}-4-(2-methoxy-phenyl)-1-methyl-piperazin-1-ium chloride, |
| 55 | 1-{4-[3-(3-bromo-phenyl)-acryloylamino]-benzyl}-1-methyl-piperidinium chloride, |
| 56 | 1-methyl-1-[3-(3-trifluoromethyl-benzoylamino)-benzyl]-piperidinium chloride, |
| 57 | 1-methyl-1-{4-[3-(3-trifluoromethyl-phenyl)-acryloylamino]-benzyl}-piperidinium chloride, |
| 58 | 4-(4-{[3-(3,4-dichloro-phenyl)-acryloylamino]-methyl}-benzyl)-4-methyl-morpholin-4-ium chloride, |
| 59 | 4-[4-(3,4-dichloro-benzoylamino)-benzyl]-4-methyl-morpholin-4-ium chloride, |
| 60 | 4-{4-[3-(3,4-dichloro-phenyl)-acryloylamino]-benzyl}-4-methyl-morpholin-4-ium chloride, |
| 61 | 4-{4-[3-(3-bromo-phenyl)-acryloylamino]-benzyl}-4-methyl-morpholin-4-ium chloride, |
| 62 | 4-methyl-4-(4-{[3-(3-trifluoromethyl-phenyl)-acryloylamino]-methyl}-benzyl)-morpholin-4-ium chloride, |
| 63 | allyl-{4-[3-(3-bromo-phenyl)-acryloylamino]-benzyl}-methyl-(tetrahydro-thiopyran-4-yl)-ammonium chloride, |
| 64 | dimethyl-(tetrahydro-pyran-4-yl)-(4-{[3-(3-trifluoromethyl-phenyl)-acryloylamino]-methyl}-benzyl)-ammonium chloride, |
| 65 | dimethyl-(tetrahydro-pyran-4-yl)-[3-(3-trifluoromethyl-benzoylamino)-benzyl]-ammonium chloride, |

| Cpd | Name |
|---|---|
| 66 | dimethyl-(tetrahydro-pyran-4-yl)-[4-(3-m-tolyl-acryloylamino)-benzyl]-ammonium chloride, |
| 67 | dimethyl-(tetrahydro-pyran-4-yl)-[4-(3-trifluoromethyl-benzoylamino)-benzyl]-ammonium chloride, |
| 68 | dimethyl-(tetrahydro-pyran-4-yl)-{4-[3-(3-trifluoromethyl-phenyl)-acryloylamino]-benzyl}-ammonium chloride, |
| 69 | dimethyl-[4-(3-methyl-benzoylamino)-benzyl]-(tetrahydro-pyran-4-yl)-ammonium chloride, |
| 70 | cycloheptyl-[4-(3,4-dichloro-benzoylamino)-benzyl]-dimethyl-ammonium chloride, |
| 71 | cyclohexyl-{4-[3-(3,4-dichloro-phenyl)-acryloylamino]-benzyl}-dimethyl-ammonium chloride, |
| 72 | {4-[3-(3-bromo-phenyl)-acryloylamino]-benzyl}-cyclohexyl-dimethyl-ammonium chloride, |
| 73 | [4-(3-bromo-benzoylamino)-benzyl]-cyclohexyl-dimethyl-ammonium chloride, |
| 74 | cyclohexyl-dimethyl-[4-(3-trifluoromethyl-benzoylamino)-benzyl]-ammonium chloride, |
| 75 | cyclohexyl-[4-(3,4-dichloro-benzoylamino)-benzyl]-dimethyl-ammonium chloride, |
| 76 | [4-(3-chloro-4-fluoro-benzoylamino)-benzyl]-cyclohexyl-dimethyl-ammonium chloride, |
| 77 | cyclohexyl-[4-(2,3-dichloro-benzoylamino)-benzyl]-dimethyl-ammonium chloride, |
| 78 | cyclohexyl-[4-(2,6-dichloro-benzoylamino)-benzyl]-dimethyl-ammonium chloride, |
| 79 | [4-(3-chloro-4-methoxy-benzoylamino)-benzyl]-cyclohexyl-dimethyl-ammonium chloride, |
| 80 | [4-(3-chloro-4-methyl-benzoylamino)-benzyl]-cyclohexyl-dimethyl-ammonium chloride, |
| 81 | cyclohexyl-[4-(2,5-dichloro-benzoylamino)-benzyl]-dimethyl-ammonium chloride, |
| 82 | cyclopentyl-[4-(3,4-dichloro-benzoylamino)-benzyl]-dimethyl-ammonium chloride, |
| 83 | cyclohexyl-{3-[3-(3,4-dichloro-phenyl)-acryloylamino]-benzyl}-dimethyl-ammonium chloride, |
| 84 | cyclohexyl-{3-[3-(4-fluoro-phenyl)-acryloylamino]-benzyl}-dimethyl-ammonium chloride, |
| 85 | dimethyl-(tetrahydro-pyran-4-yl)-{4-[(4'-trifluoromethyl-biphenyl-3-carbonyl)-amino]-benzyl}-ammonium chloride, |
| 86 | cyclohexyl-dimethyl-{4-[(4'-methyl-biphenyl-3-carbonyl)-amino]-benzyl}-ammonium chloride, |
| 87 | dimethyl-{4-[(4'-methyl-biphenyl-3-carbonyl)-amino]-benzyl}-(tetrahydro-pyran-4-yl)-ammonium chloride, |
| 88 | {4-[(biphenyl-4-carbonyl)-amino]-benzyl}-dimethyl-(tetrahydro-pyran-4-yl)-ammonium chloride, |
| 89 | dimethyl-{4-[(naphthalene-1-carbonyl)-amino]-benzyl}-(tetrahydro-pyran-4-yl)-ammonium chloride, |
| 90 | dimethyl-{4-[(naphthalene-2-carbonyl)-amino]-benzyl}-(tetrahydro-pyran-4-yl)-ammonium chloride, |
| 91 | ethyl-methyl-{4-[(naphthalene-2-carbonyl)-amino]-benzyl}-(tetrahydro-pyran-4-yl)-ammonium chloride, |
| 92 | methyl-{4-[(naphthalene-2-carbonyl)-amino]-benzyl}-propyl-(tetrahydro-pyran-4-yl)-ammonium chloride, |
| 93 | {4-[(7-bromo-naphthalene-2-carbonyl)-amino]-benzyl}-dimethyl-(tetrahydro-pyran-4-yl)-ammonium chloride, |
| 94 | {4-[(7-bromo-naphthalene-2-carbonyl)-amino]-benzyl}-cyclohexyl-dimethyl-ammonium chloride, |
| 95 | {4-[(6-bromo-2H-chromene-3-carbonyl)-amino]-benzyl}-dimethyl-(tetrahydro-pyran-4-yl)-ammonium chloride, |
| 96 | {4-[(6-chloro-2H-chromene-3-carbonyl)-amino]-benzyl}-dimethyl-(tetrahydro-pyran-4-yl)-ammonium chloride, |
| 97 | {4-[(6-bromo-2H-chromene-3-carbonyl)-amino]-benzyl}-cyclohexyl-dimethyl-ammonium chloride, |
| 98 | {4-[(6-chloro-2H-chromene-3-carbonyl)-amino]-benzyl}-cyclohexyl-dimethyl-ammonium chloride, |
| 99 | (4-{[(6-bromo-2H-chromene-3-carbonyl)-amino]-methyl}-benzyl)-dimethyl-(tetrahydro-pyran-4-yl)-ammonium chloride, |
| 100 | {4-[(5,7-dichloro-2H-chromene-3-carbonyl)-amino]-benzyl}-dimethyl-(tetrahydro-pyran-4-yl)-ammonium chloride, |
| 101 | cyclohexyl-{4-[(5,7-dichloro-2H-chromene-3-carbonyl)-amino]-benzyl}-dimethyl-ammonium chloride, |
| 102 | {4-[(6,8-dichloro-2H-chromene-3-carbonyl)-amino]-benzyl}-dimethyl-(tetrahydro-pyran-4-yl)-ammonium chloride, |
| 103 | dimethyl-{4-[(6-methyl-2H-chromene-3-carbonyl)-amino]-benzyl}-(tetrahydro-pyran-4-yl)-ammonium chloride, |
| 104 | {4-[(6-methoxy-2H-chromene-3-carbonyl)-amino]-benzyl}-dimethyl-(tetrahydro-pyran-4-yl)-ammonium chloride, |

-continued

| Cpd | Name |
|---|---|
| 105 | cyclohexyl-dimethyl-{4-[(6-methyl-2H-chromene-3-carbonyl)-amino]-benzyl}-ammonium chloride, |
| 106 | cyclohexyl-{4-[(6-methoxy-2H-chromene-3-carbonyl)-amino]-benzyl}-dimethyl-ammonium chloride, |
| 107 | cyclohexyl-{4-[(6,8-dichloro-2H-chromene-3-carbonyl)-amino]-benzyl}-dimethyl-ammonium chloride, |
| 108 | (2R)-{4-[(6-chloro-2H-chromene-3-carbonyl)-amino]-benzyl}-dimethyl-(tetrahydro-furan-2-ylmethyl)-ammonium chloride, |
| 109 | (2S)-{4-[(6-chloro-2H-chromene-3-carbonyl)-amino]-benzyl}-dimethyl-(tetrahydro-furan-2-ylmethyl)-ammonium chloride, |
| 110 | (2S)-bicyclo[2.2.1]hept-2-yl-{4-[(6-chloro-2H-chromene-3-carbonyl)-amino]-benzyl}-dimethyl-ammonium chloride, |
| 111 | bicyclo[2.2.1]hept-2-yl-{4-[(6,8-dichloro-2H-chromene-3-carbonyl)-amino]-benzyl}-dimethyl-ammonium chloride, |
| 112 | dimethyl-{4-[(8-methyl-2H-chromene-3-carbonyl)-amino]-benzyl}-(tetrahydro-pyran-4-yl)-ammonium chloride, |
| 113 | cyclohexyl-dimethyl-{4-[(8-methyl-2H-chromene-3-carbonyl)-amino]-benzyl}-ammonium chloride, |
| 114 | {4-[(6-chloro-8-methyl-2H-chromene-3-carbonyl)-amino]-benzyl}-cyclohexyl-dimethyl-ammonium chloride, |
| 115 | {4-[(6-chloro-8-methyl-2H-chromene-3-carbonyl)-amino]-benzyl}-dimethyl-(tetrahydro-pyran-4-yl)-ammonium chloride, |
| 116 | cyclohexyl-{4-[(7,8-dichloro-2H-chromene-3-carbonyl)-amino]-benzyl}-dimethyl-ammonium chloride, |
| 117 | bicyclo[2.2.1]hept-2-yl-{4-[(6-chloro-8-methyl-2H-chromene-3-carbonyl)-amino]-benzyl}-dimethyl-ammonium chloride, |
| 118 | {4-[(6-chloro-8-methyl-2H-chromene-3-carbonyl)-amino]-benzyl}-cycloheptyl-dimethyl-ammonium chloride, |
| 119 | {4-[(6-chloro-8-methyl-2H-chromene-3-carbonyl)-amino]-benzyl}-cyclopentyl-dimethyl-ammonium chloride, |
| 120 | {4-[(6-chloro-8-methyl-2H-chromene-3-carbonyl)-amino]-benzyl}-dimethyl-(tetrahydro-thiophen-3-yl)-ammonium chloride, |
| 121 | (4-{[(6-chloro-8-methyl-2H-chromene-3-carbonyl)-amino]-methyl}-benzyl)-dimethyl-(tetrahydro-pyran-4-yl)-ammonium chloride, |
| 122 | {4-[(6,8-dichloro-2H-chromene-3-carbonyl)-amino]-benzyl}-dimethyl-(tetrahydro-thiophen-3-yl)-ammonium chloride, |
| 123 | cyclohexyl-{4-[(6-fluoro-2H-chromene-3-carbonyl)-amino]-benzyl}-dimethyl-ammonium chloride, |
| 124 | cyclohexyl-{4-[(5-fluoro-2H-chromene-3-carbonyl)-amino]-benzyl}-dimethyl-ammonium chloride, |
| 125 | cyclohexyl-dimethyl-{4-[(6-trifluoromethyl-2H-chromene-3-carbonyl)-amino]-benzyl}-ammonium chloride, |
| 126 | cyclohexyl-{4-[(8-fluoro-2H-chromene-3-carbonyl)-amino]-benzyl}-dimethyl-ammonium chloride, |
| 127 | cyclohexyl-dimethyl-{4-[(7-methyl-2H-chromene-3-carbonyl)-amino]-benzyl}-ammonium chloride, |
| 128 | cyclohexyl-{4-[(7-methoxy-2H-chromene-3-carbonyl)-amino]-benzyl}-dimethyl-ammonium chloride, |
| 129 | {4-[(6-tert-butyl-2H-chromene-3-carbonyl)-amino]-benzyl}-cyclohexyl-dimethyl-ammonium chloride, |
| 130 | dimethyl-(tetrahydro-thiophen-3-yl)-{4-[(6-trifluoromethyl-2H-chromene-3-carbonyl)-amino]-benzyl}-ammonium chloride, |
| 131 | {4-[(5-fluoro-2H-chromene-3-carbonyl)-amino]-benzyl}-dimethyl-(tetrahydro-thiophen-3-yl)-ammonium chloride, |
| 132 | {4-[(6-fluoro-2H-chromene-3-carbonyl)-amino]-benzyl}-dimethyl-(tetrahydro-thiophen-3-yl)-ammonium chloride, |
| 133 | cyclohexyl-dimethyl-{4-[(5-trifluoromethyl-2H-chromene-3-carbonyl)-amino]-benzyl}-ammonium chloride, |
| 134 | cyclohexyl-dimethyl-{4-[(8-trifluoromethyl-2H-chromene-3-carbonyl)-amino]-benzyl}-ammonium chloride, |
| 135 | {4-[(3H-benzo[f]chromene-2-carbonyl)-amino]-benzyl}-dimethyl-(tetrahydro-pyran-4-yl)-ammonium chloride, |
| 136 | 1-{4-[(3H-benzo[f]chromene-2-carbonyl)-amino]-benzyl}-1-methyl-pyrrolidinium chloride, |
| 137 | {4-[(3H-benzo[f]chromene-2-carbonyl)-amino]-benzyl}-cyclohexyl-dimethyl-ammonium chloride, |
| 138 | {4-[(3H-benzo[f]chromene-2-carbonyl)-amino]-benzyl}-dimethyl-(tetrahydro-thiopyran-4-yl)-ammonium chloride, |
| 139 | 4-{4-[(3H-benzo[f]chromene-2-carbonyl)-amino]-benzyl}-4-methyl-morpholin-4-ium chloride, |
| 140 | {4-[(3H-benzo[f]chromene-2-carbonyl)-amino]-benzyl}-dimethyl-(tetrahydro-pyran-4-ylmethyl)-ammonium chloride, |
| 141 | (4-{[(3H-benzo[f]chromene-2-carbonyl)-amino]-methyl}-benzyl)-dimethyl-(tetrahydro-pyran-4-yl)-ammonium chloride, |
| 142 | (4-{[(3-bromo-8,9-dihydro-7H-benzocycloheptene-6-carbonyl)-amino]-methyl}-benzyl)-dimethyl-(tetrahydro-pyran-4-yl)-ammonium chloride, |
| 143 | {4-[(3-bromo-8,9-dihydro-7H-benzocycloheptene-6-carbonyl)-amino]-benzyl}-dimethyl-(tetrahydro-pyran-4-yl)-ammonium chloride, |

| Cpd | Name |
|---|---|
| 144 | {4-[(3-bromo-8,9-dihydro-7H-benzocycloheptene-6-carbonyl)-amino]-benzyl}-cyclohexyl-dimethyl-ammonium chloride, |
| 145 | 1-{4-[(8,9-dihydro-7H-benzocycloheptene-6-carbonyl)-amino-benzyl}-1-methyl-pyrrolidinium chloride, |
| 146 | cyclohexyl-{4-[(8,9-dihydro-7H-benzocycloheptene-6-carbonyl)-amino]-benzyl}-dimethyl-ammonium chloride, |
| 147 | {4-[(8,9-dihydro-7H-benzocycloheptene-6-carbonyl)-amino]-benzyl}-dimethyl-(tetrahydro-pyran-4-yl)-ammonium chloride, |
| 148 | (4-{[(8,9-dihydro-7H-benzocycloheptene-6-carbonyl)-amino]-methyl}-benzyl)-dimethyl-(tetrahydro-pyran-4-yl)-ammonium chloride, |
| 149 | dimethyl-(4-{[(2-methyl-5-phenyl-furan-3-carbonyl)-amino]-methyl}-benzyl)-(tetrahydro-pyran-4-yl)-ammonium chloride, |
| 150 | [4-({[5-(4-chloro-phenyl)-2-methyl-furan-3-carbonyl]-amino}-methyl)-benzyl]-dimethyl-(tetrahydro-pyran-4-yl)-ammonium chloride, |
| 151 | dimethyl-{4-[(2-methyl-5-phenyl-furan-3-carbonyl)-amino]-benzyl}-(tetrahydro-pyran-4-yl)-ammonium chloride, |
| 152 | {4-[(benzofuran-2-carbonyl)-amino]-benzyl}-dimethyl-(tetrahydro-pyran-4-yl)-ammonium chloride, |
| 153 | (4-{[5-(4-chloro-phenyl)-2-trifluoromethyl-furan-3-carbonyl]-amino}-benzyl)-dimethyl-(tetrahydro-pyran-4-yl)-ammonium chloride, |
| 154 | (4-{[5-(4-chloro-phenyl)-2-trifluoromethyl-furan-3-carbonyl]-amino}-benzyl)-cyclohexyl-dimethyl-ammonium chloride, |
| 155 | {4-[(5-chloro-benzofuran-2-carbonyl)-amino]-benzyl}-dimethyl-(tetrahydro-pyran-4-yl)-ammonium chloride, |
| 156 | {4-[(5-chloro-benzofuran-2-carbonyl)-amino]-benzyl}-cyclohexyl-dimethyl-ammonium chloride, |
| 157 | {4-[(benzofuran-2-carbonyl)-amino]-benzyl}-cyclohexyl-dimethyl-ammonium chloride, |
| 158 | dimethyl-{4-[(1-methyl-1H-indole-2-carbonyl)-amino]-benzyl}-(tetrahydro-pyran-4-yl)-ammonium chloride, |
| 159 | {4-[(5-chloro-1H-indole-2-carbonyl)-amino]-benzyl}-dimethyl-(tetrahydro-pyran-4-yl)-ammonium chloride, |
| 160 | {4-[(5-bromo-1H-indole-2-carbonyl)-amino]-benzyl}-dimethyl-(tetrahydro-pyran-4-yl)-ammonium chloride, |
| 161 | dimethyl-{4-[(1-methyl-1H-indole-3-carbonyl)-amino]-benzyl}-(tetrahydro-pyran-4-yl)-ammonium chloride, |
| 162 | {4-[(1-benzyl-1H-indole-3-carbonyl)-amino]-benzyl}-dimethyl-(tetrahydro-pyran-4-yl)-ammonium chloride, |
| 163 | cyclohexyl-dimethyl-{4-[(1-methyl-1H-indole-2-carbonyl)-amino]-benzyl}-ammonium chloride, |
| 164 | {4-[(5-chloro-1H-indole-2-carbonyl)-amino]-benzyl}-cyclohexyl-dimethyl-ammonium chloride, |
| 165 | (2S)-{4-[(5-chloro-1H-indole-2-carbonyl)-amino]-benzyl}-dimethyl-(tetrahydro-furan-2-ylmethyl)-ammonium chloride, |
| 166 | bicyclo[2.2.1]hept-2-ylmethyl-{4-[(5-chloro-1H-indole-2-carbonyl)-amino]-benzyl}-dimethyl-ammonium chloride, |
| 167 | {4-[(7,8-dichloro-2,3-dihydro-benzo[b]oxepine-4-carbonyl)-amino]-benzyl}-dimethyl-(tetrahydro-pyran-4-yl)-ammonium chloride, |
| 168 | cyclohexyl-{4-[(7,8-dichloro-2,3-dihydro-benzo[b]oxepine-4-carbonyl)-amino]-benzyl}-dimethyl-ammonium chloride, |
| 169 | bicyclo[2.2.1]hept-2-yl-{4-[(7,8-dichloro-2,3-dihydro-benzo[b]oxepine-4-carbonyl)-amino]-benzyl}-dimethyl-ammonium chloride, |
| 170 | (4-{[(7,8-dichloro-2,3-dihydro-benzo[b]oxepine-4-carbonyl)-amino]-methyl}-benzyl)-dimethyl-(tetrahydro-pyran-4-yl)-ammonium chloride, |
| 171 | {4-[(7,8-dichloro-2,3-dihydro-benzo[b]oxepine-4-carbonyl)-amino]-benzyl}-dimethyl-(tetrahydro-thiophen-3-yl)-ammonium chloride, |
| 172 | {4-[(5-bromo-pyridine-3-carbonyl)-amino]-benzyl}-dimethyl-(tetrahydro-pyran-4-yl)-ammonium chloride, |
| 173 | {4-[(2-chloro-pyridine-4-carbonyl)-amino]-benzyl}-dimethyl-(tetrahydro-pyran-4-yl)-ammonium chloride, |
| 174 | {4-[(3-chloro-benzo[b]thiophene-2-carbonyl)-amino]-benzyl}-dimethyl-(tetrahydro-pyran-4-yl)-ammonium chloride, |
| 175 | {4-[(2,5-dichloro-thiophene-3-carbonyl)-amino]-benzyl}-dimethyl-(tetrahydro-pyran-4-yl)-ammonium chloride, |
| 176 | {4-[(benzo[b]thiophene-2-carbonyl)-amino]-benzyl}-dimethyl-(tetrahydro-pyran-4-yl)-ammonium chloride, |
| 177 | {4-[(benzo[b]thiophene-2-carbonyl)-amino]-benzyl}-cyclohexyl-dimethyl-ammonium chloride, and |
| 178 | {4-[(3-chloro-benzo[b]thiophene-2-carbonyl)-amino]-benzyl}-cyclohexyl-dimethyl-ammonium chloride. |

DISCUSSION OF THE INVENTION

As shown in the foregoing Scheme A, the scaled-up process of the present invention differs from the process for preparing quaternary iodide salt compounds of Formula (I) disclosed in US Patent Publication 2006/0293379. The disclosed process required an ion-exchange step and the use of methyl iodide and methylene dichloride. The process described herein eliminates the ion-exchange step, does not require the use of methyl iodide and methylene dichloride and uses a reduced amount of solvents.

The present invention also relates to a process for preparing a quaternary salt compound of Formula (Ia):

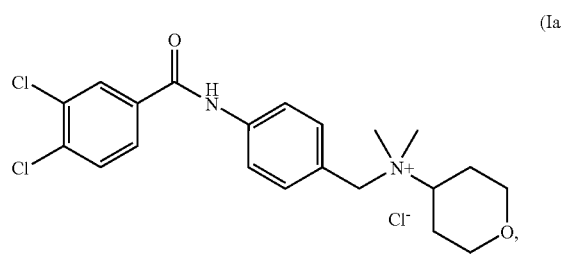

(Ia)

wherein the compound of Formula (Ia) is disclosed in US Patent Publication 2006/0293379 as [4-(3,4-dichloro-benzoylamino)-benzyl]-dimethyl-(tetrahydro-pyran-4-yl)-ammonium chloride Compound 17.

US Patent Publication 2006/029337 further discloses Example 1 as describing the preparation of a quaternary iodide salt precursor and subsequent conversion to the quaternary chloride salt [4-(3,4-dichloro-benzoylamino)-benzyl]-dimethyl-(tetrahydro-pyran-4-yl)-ammonium chloride Compound 17. The process of the present invention, though, enables the direct preparation of the quaternary ammonium chloride salt of Compound 17, labeled herein as the compound of Formula (Ia) and representative of the compounds of Formula (I) disclosed in U.S. Patent Publication 2006/029337.

Scheme B represents a process for providing a quaternary salt compound of Formula (Ia) by direct precipitation.

Scheme B

A process for preparing a quaternary salt compound of Formula (Ia):

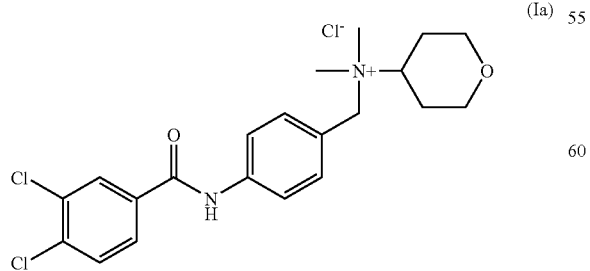

(Ia)

comprising the steps of:

Step A. reacting a Compound B1 hydrochloride salt with a Compound B2 to provide a Compound B3:

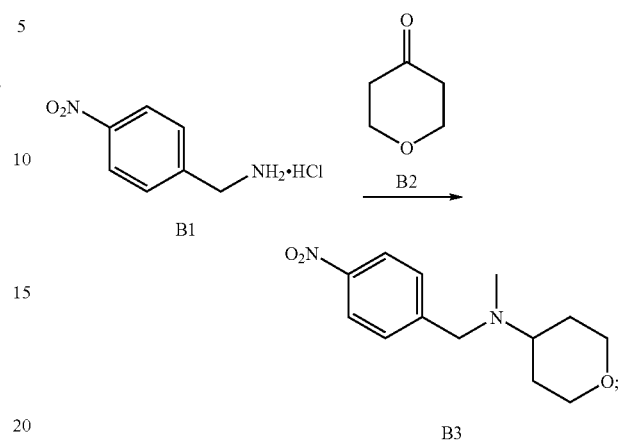

Step B. reacting Compound B3 to provide a Compound B4:

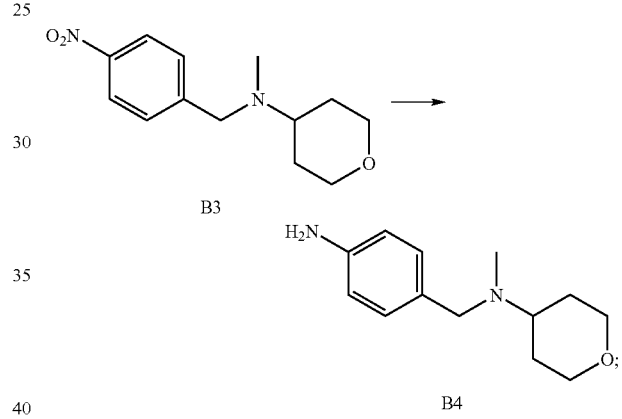

Step C. reacting Compound B4 with a Compound B5 to provide a Compound B6:

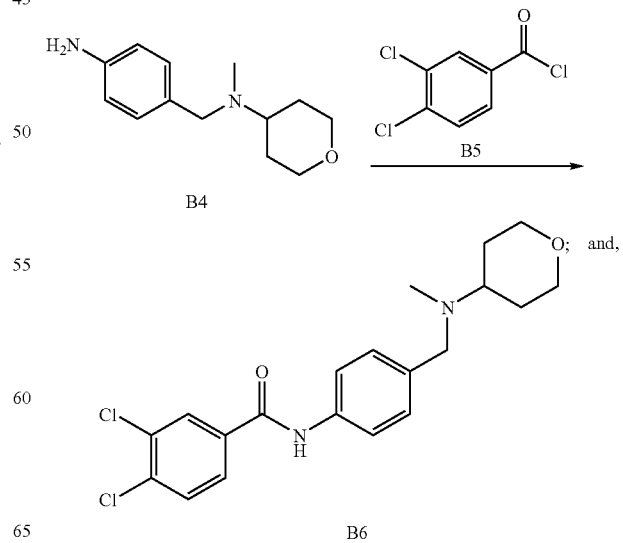

Step D. reacting Compound B6 with a chlorinated methyl Compound B7 to provide the compound of Formula (Ia):

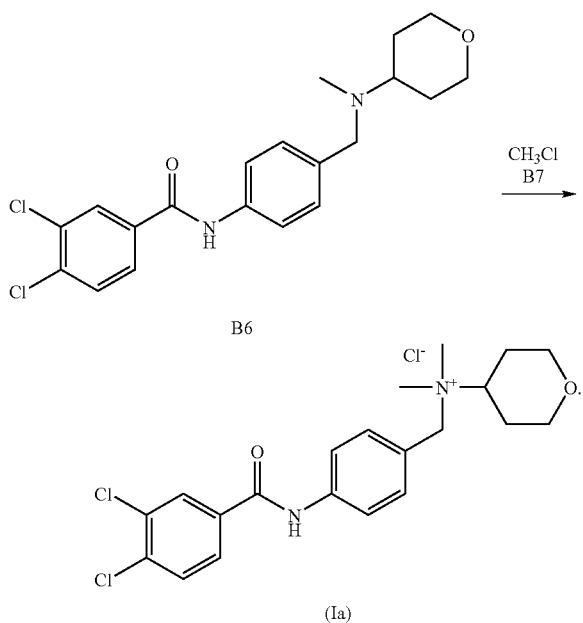

In embodiments of the present invention, Compound B6 may be recrystallized in Step C. or Step D. using a solvent selected from EtOAc, MeCN, hexanes, EtOH and the like and mixtures thereof to provide a high purity intermediate which avoids the need for purification via column chromatography.

In embodiments of the present invention, the compound of Formula (Ia) may be recrystallized in Step D. using EtOH and the like, thus also avoiding the need for purification via column chromatography.

In Step D., the reaction of Compound B6 and Compound B7 is carried out by adding Compound B7 to a solution of Compound B6 in a solvent under pressure and at an elevated temperature.

The solvent used in Step D. is selected from the group consisting of n-BuOH, toluene, IPA, EtOH, acetone, MeCN, DMF, THF and the like and mixtures thereof, wherein the reaction conditions include an elevated temperature and pressure.

In embodiments of the present invention, the solvent used in Step D. is selected from the group consisting of n-BuOH and toluene.

In embodiments of the present invention, the reaction pressure used in Step D. may be in a range of from about 10 psi to about 200 psi, or from about 10 psi to about 100 psi, or from about 10 psi to about 50 psi, or from about 10 psi to about 25 psi, or from about 20 psi to about 25 psi, or about 22 psi.

In embodiments of the present invention, the molar ratio of Compound B6:Compound B7 is from about 1:3 to about 1:8; or, from about 1:3 to about 1:5; or, about 1:3.

The foregoing schemes are offered by way of illustration; the invention should not be construed as being limited by the chemical reactions and conditions expressed. The methods for preparing the various starting materials used in the schemes are within the skill of persons versed in the art.

Chemical Definitions

Bond lines drawn into a ring system from a substituent variable indicate that the substituent may be attached to any of the substitutable ring atoms.

As used herein, the following terms are intended to have the following definitions:

The term "alkyl" means a saturated aliphatic branched or straight-chain monovalent hydrocarbon radical or linking group substituent having 1-8 carbon atoms. The term includes an alkyl substituent having 1-4 carbon atoms (i.e. lower alkyl). An alkyl radical is derived by the removal of one hydrogen atom from a carbon atom and the linking group is derived by the removal of one hydrogen atom from each of two carbon atoms in the chain. The term includes, without limitation, methyl, methylene, ethyl, ethylene, propyl, propylene, isopropyl, isopropylene, n-butyl, n-butylene, t-butyl, t-butylene, pentyl, pentylene, hexyl, hexylene and the like. An alkyl substituent may be attached to a core molecule via a terminal carbon atom or via a carbon atom within the chain. Similarly, any number of substituent variables may be attached to an alkyl substituent when allowed by available valences.

The term "alkenyl" means an alkyl radical or linking group substituent having 2-8 carbon atoms and at least one double bond derived by the removal of one hydrogen atom from each of two adjacent carbon atoms in the chain. The term includes an alkenyl substituent having 2-4 carbon atoms. The term includes, without limitation, methylidene, vinyl, vinylidene, allyl, allylidene, propylidene, isopropenyl, iso-propylidene, prenyl, prenylene (3-methyl-2-butenylene), methallyl, methallylene, allylidene (2-propenylidene), crotylene (2-butenylene), and the like. An alkenyl substituent may be attached to a core molecule via a terminal carbon atom or via a carbon atom within the chain. Similarly, any number of substituent variables may be attached to an alkenyl substituent when allowed by available valences.

The term "alkoxy" means an alkyl radical or linking group substituent attached through an oxygen-linking atom, wherein the radical is of the formula —O-alkyl and a linking group is of the formula —O-alkyl-. The term includes, without limitation, methoxy, ethoxy, propoxy, butoxy and the like. An alkoxy substituent may be attached to a core molecule and further substituted where allowed by available valences.

The term "cycloalkyl" means a saturated or partially unsaturated monocyclic, polycyclic or bridged hydrocarbon ring system radical or linking group. A ring of 3 to 20 carbon atoms may be designated by $C_{3-20}$ cycloalkyl; a ring of 3 to 12 carbon atoms may be designated by $C_{3-12}$ cycloalkyl, a ring of 3 to 8 carbon atoms may be designated by $C_{3-8}$ cycloalkyl and the like. A cycloalkyl substituent may be attached to a core molecule and further substituted where allowed by available valences.

The term cycloalkyl includes, without limitation, cyclopropyl, cyclobutyl, cyclopentyl, cyclohexyl, cyclohexenyl, cycloheptyl, cyclooctyl, indanyl, indenyl, 1,2,3,4-tetrahydronaphthalenyl, 5,6,7,8-tetrahydro-naphthalenyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantanyl, octahydro-4,7-methano-1H-indenyl, octahydro-2,5-methano-pentalenyl (also referred to as hexahydro-2,5-methano-pentalenyl) and the like.

The term "aryl" means an unsaturated, conjugated π electron monocyclic or polycyclic hydrocarbon ring system radical or linking group substituent of 6, 9, 10 or 14 carbon atoms. The term includes, without limitation, phenyl, naphthalenyl, fluorenyl, azulenyl, anthracenyl and the like. An aryl substituent may be attached to a core molecule and further substituted where allowed by available valences.

The term heterocyclyl includes, without limitation, furanyl, thienyl, 2H-pyrrolyl, 2-pyrrolinyl, 3-pyrrolinyl, pyrrolidinyl, pyrrolyl, 1,3-dioxolanyl, oxazolyl, thiazolyl, imidazolyl, 2-imidazolinyl (also referred to as 4,5-dihydro-1H-imidazolyl), imidazolidinyl, 2-pyrazolinyl, pyrazolidinyl, pyrazolyl, isoxazolyl, isothiazolyl, oxadiazolyl, triazolyl, thiadiazolyl, tetrazolyl, tetrazolinyl, tetrazolidinyl, 2H-pyranyl, 4H-pyranyl, thiopyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, azetidinyl, azepanyl, indolizinyl, indolyl, isoindolyl, 3H-indolyl, indolinyl, benzofuranyl, benzo[b]thienyl, 1H-indazolyl, benzoimidazolyl, benzothiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl, quinuclidinyl, 2H-chromenyl, 3H-benzo[f]chromenyl, tetrahydro-furanyl, tetrahydro-thienyl, tetrahydro-pyranyl, tetrahydro-thiopyranyl, tetrahydro-pyridazinyl, hexahydro-1,4-diazepinyl, hexahydro-1,4-oxazepanyl, 2,3-dihydro-benzo[b]oxepinyl, 1,3-benzodioxolyl (also known as 1,3-methylenedioxyphenyl), 2,3-dihydro-1,4-benzodioxinyl (also known as 1,4-ethylenedioxyphenyl), benzo-dihydro-furanyl (also known as 2,3-dihydro-benzofuranyl), benzo-tetrahydro-pyranyl, benzo-dihydro-thienyl, 5,6,7,8-tetrahydro-4H-cyclohepta[b]thienyl, 5,6,7-trihydro-4H-cyclohexa[b]thienyl, 5,6-dihydro-4H-cyclopenta[b]thienyl, 2-aza-bicyclo[2.2.1]heptyl, 1-aza-bicyclo[2.2.2]octyl, 8-aza-bicyclo[3.2.1]octyl, 7-oxa-bicyclo[2.2.1]heptyl, pyrrolidinium, piperidinium, piperazinium, morpholinium and the like.

The term "carbonyl" means a linking group having the formula —C(O)— or —C(=O)—.

The term "thiocarbonyl" means a linking group having the formula —C(S)— or —C(=S)—.

The term "sulfonyl" means a linking group having the formula —SO$_2$—.

The term "alkoxycarbonyl" means a radical having the formula —C(O)O-alkyl.

The term "halo" or "halogen" means one or more fluoro, chloro, bromo or iodo atom radicals.

The term "substituted" means one or more hydrogen atoms on a core molecule have been replaced with one or more radicals or linking groups, wherein the linking group, by definition is also further substituted.

The term "about", either used explicitly or impliedly preceding a quantitative value, means the approximation to said value which one skilled in the art would reasonably infer due to variations in experimental conditions and/or measurements for said value.

The substituent nomenclature used in the disclosure of the present invention was derived using IUPAC rules.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore, when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and P. G. M. Wuts and T. W. Greene, *Protective Groups in Organic Synthesis*, 4$^{th}$ Edition, John Wiley & Sons, 2007. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "geometric isomer" means isomers that differ in the orientation of substituent atoms in relationship to a carbon-carbon double bond, to a cycloalkyl ring, or to a bridged bicyclic system.

Substituent atoms (other than hydrogen) on each side of a carbon-carbon double bond may be in an E or Z configuration according to the Cahn-Ingold-Prelog system sequence rules that rank the two substituent groups at each carbon atom. In the "E" configuration, the two higher ranking substituents are on opposite sides in relationship to the carbon-carbon double bond. In the "Z" configuration, the two higher ranking substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

Accordingly, the descriptors ("R," "S," "E," and "Z") indicate isomeric atom configurations and are intended to be used as defined in the literature.

Furthermore, compounds of the present invention may have at least one crystalline, polymorph or amorphous form. The plurality of such forms are included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Synthetic Methods

Representative compounds of the present invention can be synthesized in accordance with the general synthetic schemes described herein and as illustrated more particularly in the specific examples that follow. The general schemes and specific examples are offered by way of illustration; the invention should not be construed as being limited by the described chemical reactions and reaction conditions or yields obtained. The methods for preparing the various starting materials used in the schemes and examples are well within the skill of persons versed in the art.

The following abbreviations and formulas have the indicated meanings:

| Abbreviation | Meaning |
| --- | --- |
| MeCN | acetonitrile |
| Cpd | compound |
| D.I. | deionized |
| DMF | N,N-dimethylformamide |
| EtOAc | ethyl acetate |
| Et$_2$O | diethyl ether |
| EtOH | ethanol |
| HCHO | Formaldehyde |
| HPLC | High Pressure Liquid Chromatography |
| IPA | isopropyl acohol |
| MeOH | Methanol |
| mmHg | vacuum as measured by millimeters of mercury |
| NaB(OAc)$_3$H | sodium triacetoxyborohydride |
| min(s)/hr(s)/d(s) | minute(s)/hour(s)/day(s) |
| MS | mass spectrum, refers to data shown as m/z (M + H)$^+$ |
| psi | pounds per square inch (gas) |
| RT/rt/r.t./RH | room temperature/relative humidity |
| SnCl$_2$•2H$_2$O | tin(II) chloride dihydrate |
| Et$_3$N | Triethylamine |
| THF | Tetrahydrofuran |

EXAMPLE 1

[4-(3,4-dichloro-benzoylamino)-benzyl]-dimethyl-(tetrahydro-pyran-4-yl)-ammonium chloride Compound of Formula (Ia)

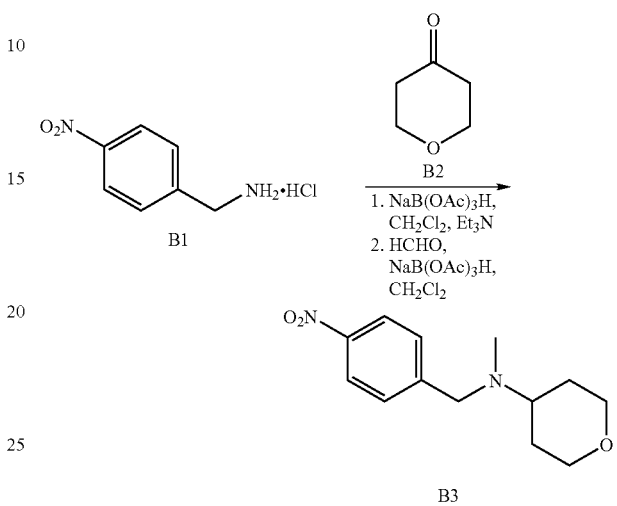

Step 1. Preparation of methyl(4-nitrobenzyl)tetrahydropyran-4-ylamine (Cpd B3)

A 3-L 4-neck round bottom flask equipped with an overhead stirrer, thermocouple, and a N$_2$ inlet adapter was charged with CH$_2$Cl$_2$ (850 mL), 4-nitrobenzylamine hydrochloride Compound B1 (72.39 g, 0.372 mol) and tetrahydro-4H-pyran-4-one Compound B2 (34.6 mL, 0.374 mol) under N$_2$. The suspension was cooled to 0° C., Et$_3$N (52.8 mL) was added and stirred for 5 min, then NaB(OAc)$_3$H (116.4 g, 0.522 mol) was added. The reaction mixture was allowed to warm to 20° C. and stirred for 6 h. A large volume of gas was released from the mixture between 12-18° C. as the mixture warmed. The reaction was monitored to completion by HPLC.

The reaction was cooled to 0° C., formaldehyde (30.22 mL) was added, then NaB(OAc)$_3$H (4×29.1 g, 0.522 mol) was added portion-wise over a 10-min period. The reaction was warmed to 20° C. and stirred for an additional 16 hrs. The reaction mixture was cooled to 0° C., then treated with 2 N NaOH solution (1350 mL). The alkaline solution was extracted with CH$_2$Cl$_2$ (850 mL×2) and the combined organic phase was washed with brine (850 mL×2) and dried over MgSO$_4$. After filtration, the solvent was condensed in vacuo to give Compound B3 (98.6 g, 106% yield, 98% area by HPLC), which was used without further purification in the next step.

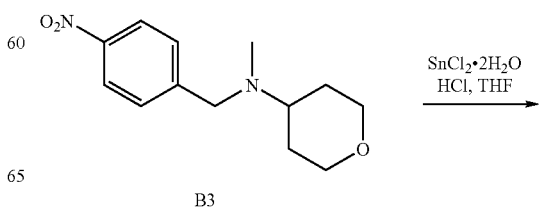

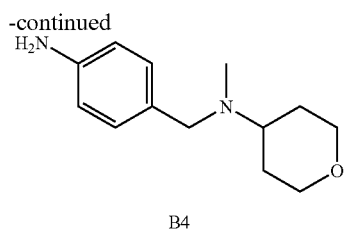

B4

Step 2. Preparation of methyl(4-aminobenzyl)tetrahydropyran-4-ylamine (Cpd B4)

A 5-L 4-neck flask equipped with an overhead stirrer, thermocouple, pressure equalization dropping funnel and a $N_2$ inlet adapter was charged with a solution of Compound B3 (98.0 g, 0.392 mol) in THF (180 mL). The solution was cooled to 6° C. in a ice-water bath. A solution of tin(II) chloride dihydrate (284.6 g, 1.262 mol) in HCl (about 37.3%, 250 mL) was added dropwise over a 40-min period, resulting in a final internal temperature of about 28° C.

After the addition, the water bath was removed and the reaction was allowed to stir at 20° C. for 2 hrs. The reaction mixture was diluted with THF (890 mL) and D.I. $H_2O$ (720 mL), then cooled to 0° C. and treated with 5 N NaOH solution (1275 mL) to a pH of about 12. After the phase separation, the aqueous phase was extracted with EtOAc (1.0 L×2). The combined organic phase was washed with brine (800 mL) and dried over $MgSO_4$. After filtration, the solvent was condensed in vacuo to give Compound B4 (83.43 g, 97% yield, 89% area by HPLC), which was used in the next step without further purification.

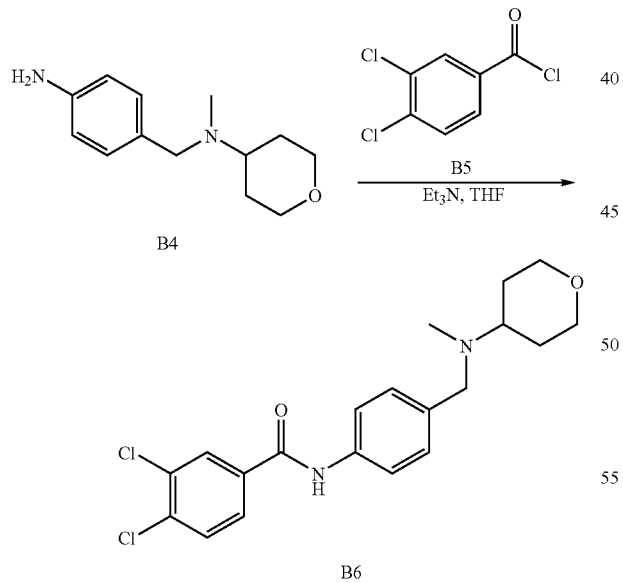

Step 3. Preparation of 3,4-dichloro-N-(4-{[methyl(tetrahydro-pyran-4-yl)amino]methyl}-phenyl)benzamide (Cpd B6)

A 5-L 4-neck flask equipped with an overhead stirrer, thermocouple, pressure-equalization dropping funnel and a $N_2$ inlet adapter was charged with THF (1000 mL), Compound B4 (82.4 g, 0.375 mol) and $Et_3N$ (104.4 mL, 0.749 mol) and stirred under $N_2$. The mixture was cooled to 2° C. in an ice-water bath and a solution of 3,4-dichlorobenzoyl chloride Compound B5 (85.7 g, 0.397 mol) in THF (300 mL) was added dropwise over a 45-min period, resulting in a final internal temperature of about 8° C. After the addition, the cooling bath was removed and the reaction mixture was allowed to stir at 20° C. for 20 hrs, then cooled to 0° C., treated with 2 N NaOH solution (800 mL) to a pH of about 13 and stirred for 5 min. After extraction using EtOAc (1.2 L×2), the combined organic phases were washed with brine (1000 mL×3) and dried over $MgSO_4$. The solvent was condensed in vacuo to give a yellowish crude product (152.4 g, 104% yield, 95.5% area by HPLC), which was recrystallized in a mixture of EtOAc/hexane (680 mL/400 mL) to afford Compound B6 (126.6 g, 86% isolated yield, 99.6% area by HPLC). The mother liquor was concentrated to give a thick material (32.6 g), which contained 53% of Compound B6 by HPLC analysis.

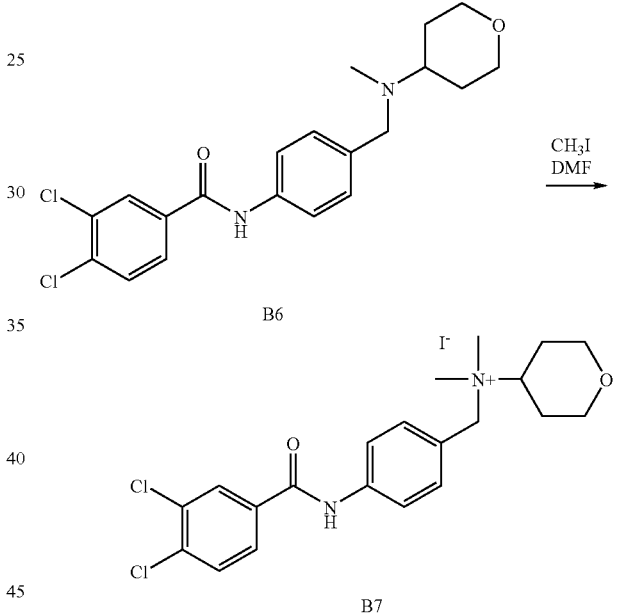

Step 4. Preparation of [4-(3,4-dichloro-benzoylamino)-benzyl]-dimethyl-(tetrahydro-pyran-4-yl)-ammonium iodide (Cpd B7)

A 2-L 4-neck flask equipped with an overhead stirrer, thermocouple, pressure-equalization dropping funnel and a $N_2$ inlet adapter was charged with DMF (600 mL) and Compound B6 (110.0 g, 0.281 mol). The reaction mixture was stirred under $N_2$ and cooled to 0° C., then iodomethane (43.7 mL, 0.702 mol) was added dropwise over a 5-min period, resulting in a final internal temperature of about 6° C. After the addition, the cooling bath was removed, and the reaction was allowed to stir at 20° C. for 20 hrs.

The solvent was removed in vacuo at 68° C. under high vacuum (about 100 mmHg). The resulting crude product was suspended in a mixture of $Et_2O$/EtOAc (1000 mL/250 mL) and stirred vigorously for 1 hr at 20° C. The solid was filtered, then washed with $Et_2O$:EtOAc (4:1 mixture, 400 mL:100 mL) and dried under house vacuum for 20 hrs to provide Compound B7 (148.6 g, 99% isolated yield, 99.3% area by HPLC) as a light yellow powdery solid. Analysis calc'd for $C_{21}H_{25}N_2O_3Cl_2I$ 0.19 $H_2O$ (538.67 MW): C, 46.82; H, 4.75; N, 5.20; Cl, 13.16; I, 23.56. Found: C, 47.11; H, 4.58; N, 5.24; Cl, 13.06; I, 23.26. Karl Fisher analysis: calc'd % $H_2O$, 0.64. found % $H_2O$, 0.65.

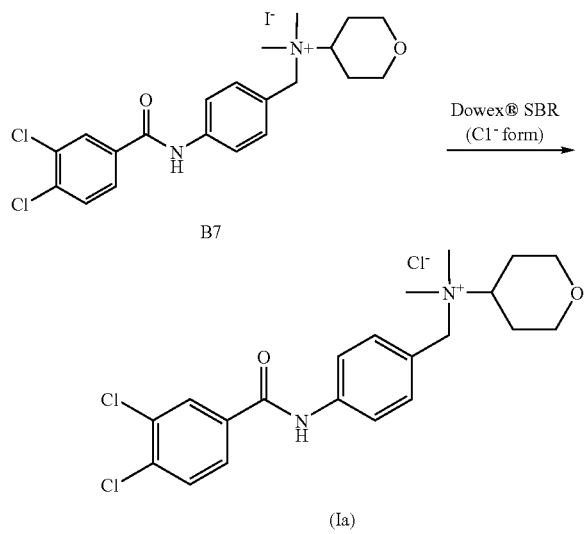

Step 5. Preparation of [4-(3,4-dichloro-benzoylamino)-benzyl]-dimethyl-(tetrahydro-pyran-4-yl)-ammonium chloride Cpd (Ia)

Dowex® SBR (Cl⁻ form, Type I, spherical beads, 16-50 mesh) anion exchange resin (3000 g) was placed in a 4-L Erlenmeyer flask and allowed to soak in a solution of MeOH/D.I. $H_2O$ (1/1, 2.0 L) for 20 h at 20° C. Compared to the amount of Compound B7 used, the resin used was about 12 times in excess. The resin was loaded into a 2-L flash chromatographic column and washed with a solution of MeOH/D.I. $H_2O$ (3/1, 2.0 L). Compound B7 (100.0 g) was dissolved in 8.0 L of MeOH/D.I. $H_2O$ (3/1) to provide a homogeneous clear solution. The solution of Compound B7 (8.0 L) was allowed to pass through the column slowly (at a 22.0 mL/min flow rate). After loading the solution of Compound B7, the column was eluted with an additional 4.0 L of MeOH/D.I. $H_2O$ (3/1) mixture. The fractions (800 mL/each) were collected, combined and condensed in vacuo at 65° C. under high vacuum.

Without an iodide detector, Compound B7 could not be distinguished from the product compound of Formula (Ia). The chromatography took about 8 h to complete and another 8 h to evaporate the solvents. The resulting wet product was chased with MeOH (600 mL×3) and dried at 50° C. under high vacuum (about 10 mmHg) for 20 h. The product compound of Formula (Ia) was obtained (85.0 g, >99% isolated yield, 99.8% area by HPLC) as an off-white solid. Analysis calc'd for $C_{21}H_{25}N_2O_3Cl_3$·0.38 $H_2O$ (MW=450.65): C, 55.97; H, 5.76; N, 6.22; Cl, 23.60. Found: C, 55.91; H, 5.55; N, 6.01; Cl, 23.80; I, <0.3. Karl Fisher analysis: calc'd % $H_2O$, 1.52. found % $H_2O$, 1.22.

Discussion of Results

The preparation of the compound of Formula (Ia) in Example 1 provided an overall yield of 81% compared to 58% by the route of Example 2. The amount of Compound B1 (0.372 mol) in Example 1 was later scaled to 0.191 mol with reproducible yields (86-99%).

Recrystallization of Compound B6 in Step 3 provided a high purity (99.6%, HPLC area %) intermediate, which eliminated the need for purification via column chromatography from the synthetic process. The reaction concentration in Step 4 was improved from 2% (originally in a mixture of acetone and MeCN) to 35% (in DMF), which resulted in quantitative quaternary salt formation and significantly reduced the generation of waste solvent. Although the Dowex® SBR resin (Cl⁻ form; reference: *J. Med. Chem.* 2000, 43, 2049-2063) used in Step 5 is typically used for low quality industrial water treatment, the use of the resin in Step 5 of Example 1 performed a complete replacement of I⁻ with Cl⁻. A suggested ion exchange resin appropriate for pharmaceutical use would be Dowex®1×4 Anion Resin (Cl⁻ form).

Although Example 1 provides a scaled-up process for preparing quaternary salt compounds of Formula (I) with a relatively higher yield over the process of Example 2, the inventors of the present invention envisaged a more efficient and less hazardous synthetic design, as shown in Example 2, which avoided the use of a large quantity of iodomethane ($CH_3I$) as used in Step 4 of Example 1 and the use of the ion-exchange column as used in Step 5 of Example 1 (see Bolt H M, Mechanisms of Carcinogenicity of Methyl Halides, *Critical Reviews in Toxicology,* 1993, 23(3), 237-53).

EXAMPLE 2

[4-(3,4-dichloro-benzoylamino)-benzyl]-dimethyl-(tetrahydro-pyran-4-yl)-ammonium chloride Compound of Formula (Ia)

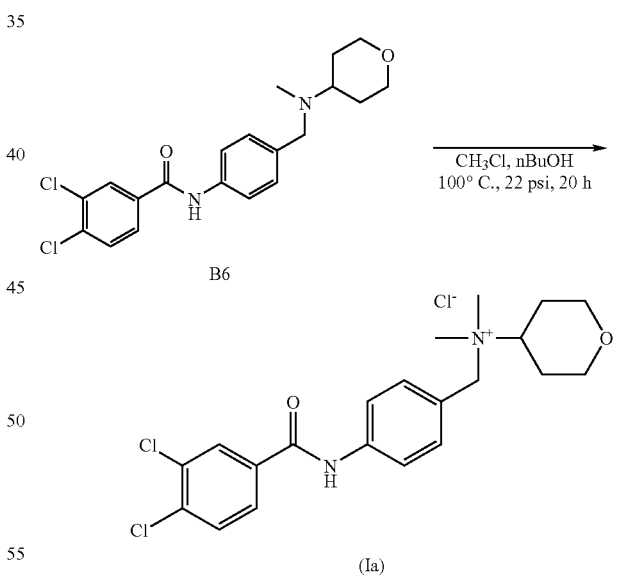

A 100-mL pressure vessel (ChemGlass), equipped with a magnetic stirrer and a pressure gauge, was connected to a Dry-Ice® condenser. A $CH_3Cl$ (chloromethane) steel cylinder (controlled by a regulator, Aldrich catalog #: Z14670-6) was connected to the Dry-Ice® condenser, then both the pressure vessel and condenser were cooled to less than −60° C. with Dry-Ice® in acetone. Compound B6 (1.0 g, 2.551 mmol, 1.0 Equiv) in nBuOH (20 mL) and $CH_3Cl$ (3.0 g, 59.42 mmol, 23.3 Equiv) from the steel cylinder via the Dry-Ice® condenser were carefully added to the vessel. The vessel was closed tightly, pressure was raised to 22 psi and the mixture was heated to 100° C. with stirring for 20 hrs. Upon completion, the reaction was cooled to 0° C. and the vessel pressure was reduced to about 0.3 psi.

The vessel was opened and the reaction mixture was stirred at 20° C. with a $N_2$ purge for 20 min. The solvent was removed in vacuo to give a crude product (1.21 g, 62%) as analyzed by HPLC. This crude material was dissolved in EtOH (200 proof, 10 mL) at 80° C., cooled to 20° C. and allowed to stand for 20 h after seeding. The solid was collected by filtration, washed with EtOAc/$Et_2O$ (10 mL, 1/3) and dried at 20° C. under house vacuum for 20 h to afford the product compound of Formula (Ia) (0.26 g, 22% isolated yield, 99.0% area by HPLC) as an off-white solid. As shown in Table 1, Entry 6.

The $^1$HNMR and LC-MS spectrum were identical to the compound of Formula (Ia) made in Step 5 by the anion exchange route. Analysis calc'd for $C_{21}H_{25}N_2O_3Cl_3 \cdot 0.38 H_2O$ (450.65 MW): C, 55.97; H, 5.76; N, 6.22; Cl, 23.60. Found: C, 55.91; H, 5.55; N, 6.01; Cl, 23.80; I, <0.3. Karl Fisher analysis: calc'd % $H_2O$, 1.52. found % $H_2O$, 1.22.

A number of solvents/solvent mixtures/phase transfer catalysts/conditions were investigated for use in the reaction and are summarized in Table 1. The amount of Compound B6 used (B6) is shown in gms, the amount of $CH_3Cl$ used is shown in gms/Equivalents, the solvents and mixture ratios used are shown in mL, the reaction temperature is shown in ° C., the reaction time is shown in hours (h), the system pressure is shown in pounds per square inch (psi), the percent Area (% starting material/% product) compared reaction materials Compound B6 relative to the product compound of Formula (Ia).

Discussion of Results

The results demonstrated in Example 2 (Table 1, Entry 6) indicate that Compound B6 having a 1:3 molar ratio with $CH_3Cl$, reacted in n-BuOH can be converted directly to the compound of Formula (Ia) by reaction at an elevated temperature and pressure. Also, the results demonstrated that the pure compound of Formula (Ia) can be obtained after crystallization of the crude mixture in EtOH, thus avoiding chromatographic purification. Additionally, the results demonstrated in Table 1 for other solvents/solvent mixtures/conditions indicate that Compound B6 can be converted to the compound of Formula (Ia) by reaction with $CH_3Cl$ using various solvents/solvent mixtures depending on the reaction temperature and pressure conditions.

As shown in Example 2, a reaction condition temperature and pressure of 100° C. and 22 psi in n-BuOH obtained a 62% yield. It is contemplated that, since n-BuOH has a boiling point of 117.73° C. under standard temperature and pressure, the reaction temperature could be further elevated to obtain an increased yield. Accordingly, the solvents capable of use in the instant process may be selected from the group consisting of n-BuOH, toluene, IPA, EtOH, acetone, MeCN, DMF, THF and the like and mixtures thereof when the reaction is run under elevated temperature and pressure conditions.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

TABLE 1

| Entry | B6 | $CH_3Cl$ | Solvents | temp | time | press | Area |
|---|---|---|---|---|---|---|---|
| 1 | 2.0 | 5.0/19 | Acetone:MeCN (125:50) | 20 | 18 | 3.8 | 92.1/2.7 (*no new impurity was determined) |
| 2 | 2.0 | 3.0/12 | IPA:NaOH (1.0 N) (125:5 mg) | 20 | 18 | 3.0 | 89.8/0.9 (*two new impurities were determined) |
| 3 | 2.0 | 8.0/31 | Acetone:MeCN (125:50) | 50 | 5 | 15 | 89.8/9.2 (no new impurity was determined) |
| 4 | 2.0 | 8.0/31 | IPA:$Et_4N^+Cl^-$ (125:70 mg) | 60 | 5 | 16.6 | 88.4/2.4 (*two new impurities were determined) |
| 5 | 1.0 | 5.02/39 | DMF (8 mL) | 100 | 20 | 39-41 | 1.0/29.5 (with formation of 55.6% unknown) |
| 6 | 1.0 | 3.0/23 | n-BuOH (20 mL) | 100 | 20 | 22 | 24/62 (10% unknown) Recrystallization of this batch in EtOH gave Cpd (Ia) (0.26 g). |
| 7 | 1.0 | 3.0/23 | toluene (40 mL) | 100 | 20 | 23 | 34/60 (6% of unknown) |
| 8 | 1.0 | 3.0/23 | n-BuOH (20 mL) | 100 | 72 | 25 | 23.5/62 (10% + 3% unknown)- recrystallization of this batch in EtOH resulted in no solid Cpd (Ia). |
| 9 | 1.0 | 3.0/23 (+1.0 mole % $CH_3I$) | n-BuOH (20 mL) | 100 | 48 | 24 | 27/21 (42% + 6% unknown) |

What is claimed is:

1. A process for preparing a quaternary ammonium chloride salt compound of Formula (I):

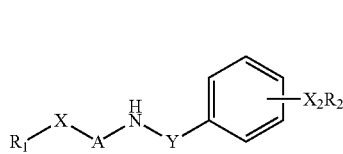

wherein
A is carbonyl, thiocarbonyl or sulfonyl;
X is a bond or —CH=CH—;
$R_1$ is selected from aryl and $C_5$-$C_{15}$cycloalkyl,
wherein aryl in $R_1$ is optionally substituted with one or more lower alkyl, —$(CH_2)_n$—$CF_3$, lower alkoxy, alkoxycarbonyl, cyano, halogen or phenyl optionally substituted by lower alkyl, —$(CH_2)_n$—$CF_3$, lower alkoxy, alkoxycarbonyl, cyano or halogen, and
wherein $C_5$-$C_{15}$cycloalkyl in $R_1$ is optionally substituted with one or more lower alkyl, —$(CH_2)_n$—$CF_3$, lower alkoxy, aryl, halogen-substituted aryl, alkoxycarbonyl, cyano or halogen;
n is 0, 1, 2, 3 or 4;
Y is a bond or —$CH_2$—;
$X_2$ is —$(CH_2)_m$—, wherein m is 1 or 2;
$R_2$ is —$N^+(R_4R_5)$—$ZR_3$;
Z is —$(CH_2)_p$— wherein p is 0, 1 or 2;
$R_3$ is selected from aryl and $C_5$-$C_{15}$cycloalkyl,
wherein aryl in $R_3$ is optionally substituted with one or more lower alkyl, —$(CH_2)_n$—$CF_3$, lower alkoxy, aryl, halogen-substituted aryl, alkoxycarbonyl, cyano or halogen, and
wherein $C_5$-$C_{15}$cycloalkyl in $R_3$ is optionally substituted with one or more lower alkyl, —$(CH_2)_n$—$CF_3$, lower alkoxy, aryl, halogen-substituted aryl, alkoxycarbonyl, cyano or halogen, and
$R_4$ and $R_5$ are each individually lower alkyl or lower alkenyl;

comprising the steps:
Step A. reacting a Compound A1 hydrochloride salt with an aldehyde or ketone Compound A2 to provide a Compound A3:

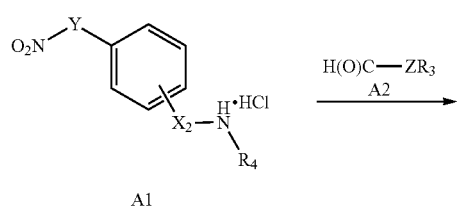

Step B. reacting Compound A3 in the presence of a metallation reagent to provide a Compound A4:

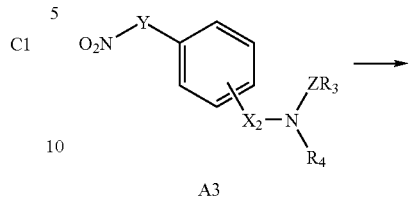

Step C. reacting Compound A4 with a Compound A5 (wherein Q represents a leaving group) to provide a Compound A6:

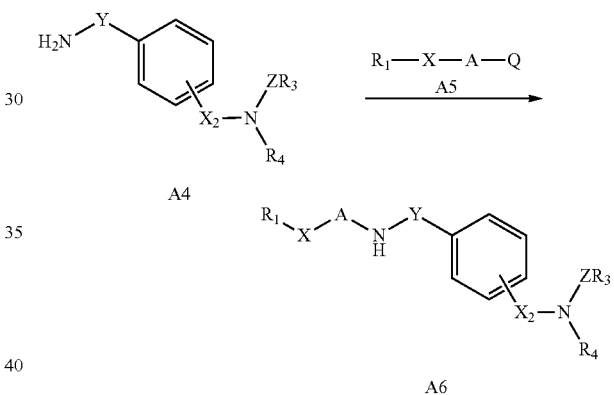

Step D.
reacting Compound A6 with a chlorinated alkyl Compound C1 to provide the Compound A9, representative of the Compound of Formula (I):

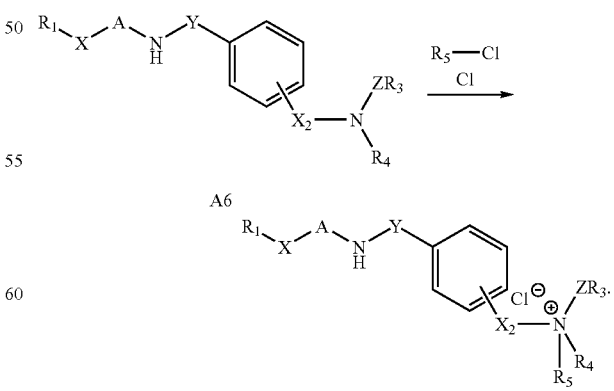

2. The process of claim 1, wherein the compound of Formula (I) is selected from the group consisting of:
- (4-{[3-(3-bromo-phenyl)-acryloylamino]-methyl}-benzyl)-cyclohexyl-dimethyl-ammonium chloride,
- {4-[(3-bromo-benzoylamino)-methyl]-benzyl}-cyclohexyl-dimethyl-ammonium chloride,
- cyclohexyl-dimethyl-{4-[(3-trifluoromethyl-benzoylamino)-methyl]-benzyl}-ammonium chloride,
- bicyclo[2.2.1]hept-2-yl-[4-(3,4-dichloro-benzoylamino)-benzyl]-dimethyl-ammonium chloride,
- cycloheptyl-[4-(3,4-dichloro-benzoylamino)-benzyl]-dimethyl-ammonium chloride,
- cyclohexyl-{4-[3-(3,4-dichloro-phenyl)-acryloylamino]-benzyl}-dimethyl-ammonium chloride,
- {4-[3-(3-bromo-phenyl)-acryloylamino]-benzyl}-cyclohexyl-dimethyl-ammonium chloride,
- [4-(3-bromo-benzoylamino)-benzyl]-cyclohexyl-dimethyl-ammonium chloride,
- cyclohexyl-dimethyl-[4-(3-trifluoromethyl-benzoylamino)-benzyl]-ammonium chloride,
- cyclohexyl-[4-(3,4-dichloro-benzoylamino)-benzyl]-dimethyl-ammonium chloride,
- [4-(3-chloro-4-fluoro-benzoylamino)-benzyl]-cyclohexyl-dimethyl-ammonium chloride,
- cyclohexyl-[4-(2,3-dichloro-benzoylamino)-benzyl]-dimethyl-ammonium chloride,
- cyclohexyl-[4-(2,6-dichloro-benzoylamino)-benzyl]-dimethyl-ammonium chloride,
- [4-(3-chloro-4-methoxy-benzoylamino)-benzyl]-cyclohexyl-dimethyl-ammonium chloride,
- [4-(3-chloro-4-methyl-benzoylamino)-benzyl]-cyclohexyl-dimethyl-ammonium chloride,
- cyclohexyl-[4-(2,5-dichloro-benzoylamino)-benzyl]-dimethyl-ammonium chloride,
- cyclopentyl-[4-(3,4-dichloro-benzoylamino)-benzyl]-dimethyl-ammonium chloride,
- cyclohexyl-{3-[3-(3,4-dichloro-phenyl)-acryloylamino]-benzyl}-dimethyl-ammonium chloride,
- cyclohexyl-{3-[3-(4-fluoro-phenyl)-acryloylamino]-benzyl}-dimethyl-ammonium chloride,
- cyclohexyl-dimethyl-{4-[(4'-methyl-biphenyl-3-carbonyl)-amino]-benzyl}-ammonium chloride,
- {4-[(7-bromo-naphthalene-2-carbonyl)-amino]-benzyl}-cyclohexyl-dimethyl-ammonium chloride,
- {4-[(3-bromo-8,9-dihydro-7H-benzocycloheptene-6-carbonyl)-amino]-benzyl}-cyclohexyl-dimethyl-ammonium chloride,
- cyclohexyl-{4-[(8,9-dihydro-7H-benzocycloheptene-6-carbonyl)-amino]-benzyl}-dimethyl-ammonium chloride.

3. The process of claim 1, wherein the reaction of Compound A1 and Compound A2 is carried out in $CH_2Cl_2$, followed by the stepwise addition of $Et_3N$ and $NaB(OAc)_3H$.

4. The process of claim 1, wherein the reaction of Compound A3 uses $SnCl_2.2H_2O$ in conc. HCl as a metallation reducing reagent THF.

5. The process of claim 1, wherein the reaction of Compound A4 and Compound A5 is carried out in a solvent mixture of $Et_3N$ in THF.

6. The process of claim 1, wherein the reaction of Compound A4 and Compound A5 is carried out by adding Compound A7 to a solution of Compound A6 in a solvent mixture such of acetone and ACN.

7. The process of claim 1, wherein the reaction of Compound A8 is carried out in an ion-exchange resin column in a solvent mixture of MeOH and water having a solvent:water ratio mix of 1:1.

8. The process according to claim 1 wherein the chlorinated alkyl compound C1 is added to Compound C6 in solution a under pressure ranging from about 15 psi to about 200 psi.

9. The process according to claim 1 where the molar ratio of Compound A1 to Compound C1 ranges from about 1:3 to about 1:8.

10. The process according to claim 1 where the reaction is conducted at a temperature from about 20° C. to about 200° C.

11. The process according to claim 1 wherein the reaction is conducted in a solvent selected from n-BUOH, toluene, IPA, EtOH, acetone, MeCN, DMF and THF.

12. The process according to claim 1 wherein Q is chloride or hydroxy.

* * * * *